(12) United States Patent
Charraud et al.

(10) Patent No.: US 12,089,716 B2
(45) Date of Patent: Sep. 17, 2024

(54) APPLICATOR WITH CARTRIDGES CONFIGURED TO DELIVER VIBRATION FOR SKIN TREATMENT

(71) Applicant: L'Oreal, Paris (FR)

(72) Inventors: Gregoire Charraud, Jersey City, NJ (US); Casey Barbarino, San Anselmo, CA (US); Rafael Feliciano, New Providence, NJ (US)

(73) Assignee: L'Oreal, Paris (FR)

( * ) Notice: Subject to any disclaimer, the term of this patent is extended or adjusted under 35 U.S.C. 154(b) by 148 days.

(21) Appl. No.: 17/733,270

(22) Filed: Apr. 29, 2022

(65) Prior Publication Data

US 2023/0346105 A1 Nov. 2, 2023

(51) Int. Cl.
*A45D 34/04* (2006.01)
*A61H 23/02* (2006.01)
*A61N 5/06* (2006.01)

(52) U.S. Cl.
CPC ........... *A45D 34/041* (2013.01); *A61H 23/02* (2013.01); *A61N 5/0616* (2013.01); *A61H 2205/022* (2013.01); *A61N 2005/0651* (2013.01); *A61N 2005/0662* (2013.01)

(58) Field of Classification Search
CPC ........... A61H 15/02; A61H 2015/0071; A61H 23/0218; A61H 2023/0227
See application file for complete search history.

(56) References Cited

U.S. PATENT DOCUMENTS

| 3,754,548 | A | * | 8/1973 | McGrath | A61H 23/0218 |
| | | | | | 601/17 |
| 8,882,685 | B2 | * | 11/2014 | Pryor | A61H 7/007 |
| | | | | | 601/19 |
| 9,144,690 | B2 | | 9/2015 | McDaniel | |
| 10,278,888 | B2 | * | 5/2019 | Sabattier | A61N 5/0616 |
| 10,334,933 | B2 | * | 7/2019 | Decaux | A61M 35/003 |
| 10,492,980 | B2 | | 12/2019 | Giraud et al. | |
| 10,667,985 | B2 | * | 6/2020 | Decaux | A61M 35/003 |
| 10,842,241 | B2 | * | 11/2020 | Casasanta, III | A45D 33/32 |

(Continued)

FOREIGN PATENT DOCUMENTS

FR 3002148 A1 8/2014
KR 200376020 Y1 * 3/2005

(Continued)

OTHER PUBLICATIONS

Search Report and Written Opinion mailed Feb. 3, 2023, issued in corresponding French Application No. FR2206220, filed Jun. 23, 2022, 6 pages.

(Continued)

*Primary Examiner* — David P Angwin
*Assistant Examiner* — Bradley S Oliver
(74) *Attorney, Agent, or Firm* — CHRISTENSEN O'CONNER JOHNSON KINDNESS PLLC

(57) ABSTRACT

A skin care system including a dispensing device configured to administer a light therapy and a vibration treatment, and an applicator configured to apply a formula, including a reservoir configured to hold the formula, a roller ball configured to apply the formula, a connection configured to attach the cartridge to the dispensing device, and a microcontroller configured to direct the dispensing device to apply the vibration treatment.

18 Claims, 4 Drawing Sheets

(56) References Cited

U.S. PATENT DOCUMENTS

| | | | | |
|---|---|---|---|---|
| 10,939,740 | B2* | 3/2021 | Cheng | A45D 40/261 |
| 11,793,586 | B2* | 10/2023 | Cheney | A61H 23/0218 |
| 2005/0015030 | A1* | 1/2005 | Bousfield | A61N 1/40 |
| | | | | 601/129 |
| 2005/0148807 | A1* | 7/2005 | Salkinder | A61N 2/12 |
| | | | | 600/9 |
| 2015/0045702 | A1* | 2/2015 | Lin | A61H 7/003 |
| | | | | 601/19 |
| 2017/0128130 | A1* | 5/2017 | Giraud | A61H 1/008 |
| 2020/0197256 | A1* | 6/2020 | Mandica | A45D 34/041 |

FOREIGN PATENT DOCUMENTS

| | | | | |
|---|---|---|---|---|
| KR | 102084761 | B1 | 3/2020 | |
| WO | 2021206244 | A1 | 10/2021 | |
| WO | WO-2022076579 | A1 * | 4/2022 | A61B 34/30 |

OTHER PUBLICATIONS

International Search Report and Written Opinion, mailed Jun. 30, 2023, issued in corresponding International Application No. PCT/US2023/017607, filed Apr. 5, 2023, 14 pages.

\* cited by examiner

APPLICATOR WITH CARTRIDGES CONFIGURED TO DELIVER VIBRATION FOR SKIN TREATMENT

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In one aspect, a skin care system comprising a dispensing device configured to administer a light therapy and an applicator configured to apply a formula, comprising a reservoir configured to hold the formula, a roller ball configured to apply the formula, a connection configured to attach the cartridge to the dispensing device, and a microcontroller configured to direct the dispensing device to apply a vibration treatment is disclosed.

In another aspect, a method of administering multiple skin treatments, using the system, the method comprising selecting an applicator filled with a formula, placing the applicator into the dispensing device, identifying a vibration treatment to apply based on the applicator, applying the formula, administering light therapy, and administering the vibration treatment is disclosed.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

While illustrative embodiments have been illustrated and described, it will be appreciated that various changes can be made therein without departing from the spirit and scope of the invention.

Described herein is an applicator configured to apply a formula to a surface, such as skin. In some embodiments, the applicator is configured to fit inside of a dispensing device. A magnet inside a roller ball in the applicator is configured to deliver vibrational therapy while the formula is applied. The dispensing device is further configured to administer a light therapy simultaneously while administering the vibration treatment and applying the formula.

Figure 1:
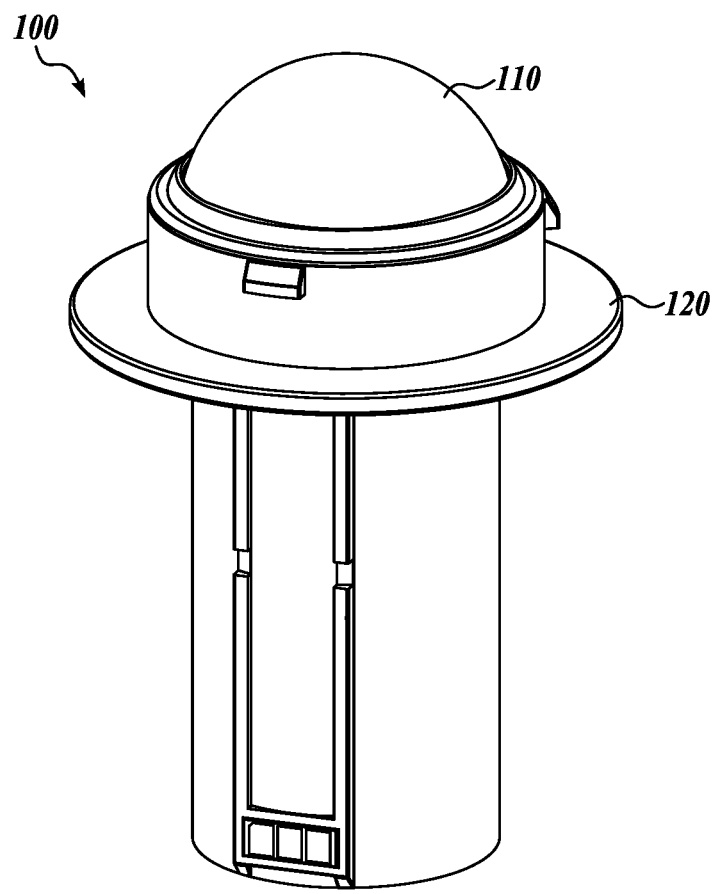
FIG. 1 is an example applicator, in accordance with the present technology.

FIG. 1 is an example applicator, in accordance with the present technology. The applicator 100 may include a roller ball 110, and an attachment 120.

Figure 2:
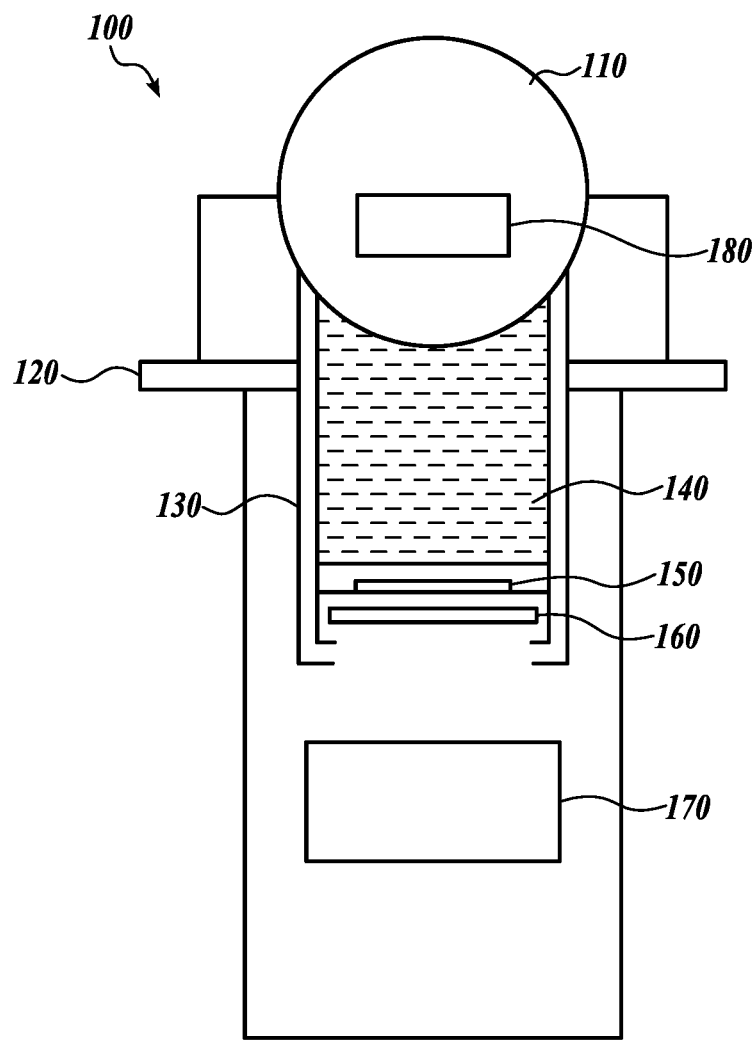
FIG. 2 is an example cross-section of an applicator, in accordance with the present technology.

The roller ball 110 may be configured to distribute and apply a formula located a reservoir inside the applicator 100 (as shown in FIG. 2). In some embodiments, the roller ball 110 is plastic, but in other embodiments, the roller ball 110 may be glass or metal.

Figure 3:
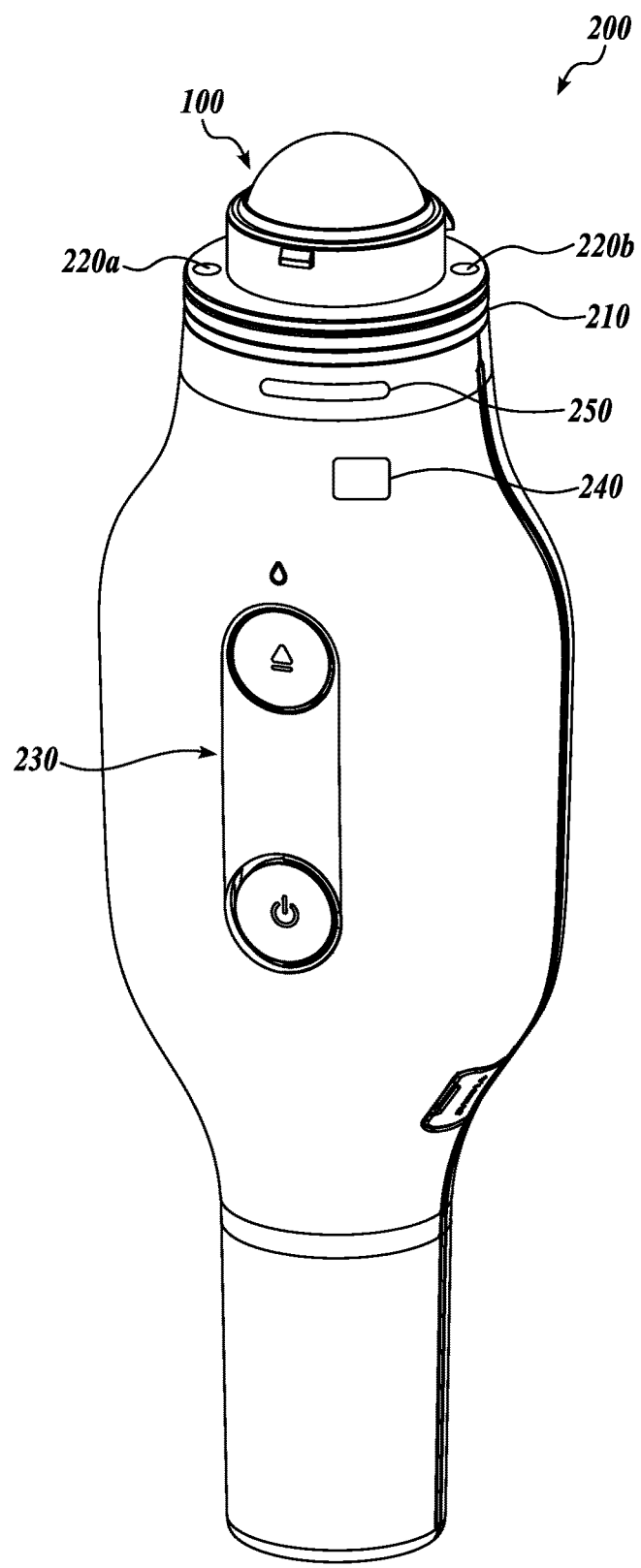
FIG. 3 is an example dispensing device, in accordance with the present technology.

In some embodiments, the applicator 100 also includes an attachment 120 configured to secure the applicator 100 into a dispensing device, such as the dispensing device 200 in FIG. 3. While the attachment 120 is illustrated as a disk shaped to couple to a dispensing device, the attachment 120 may take any form capable of securing the applicator to a dispensing device including a threaded attachment, a magnet, or an attachment configured to snap into the dispensing device. In some embodiments, the attachment 120 is clear so that the dispensing device is visible through the attachment.

In operation, the applicator 100 can be placed inside a dispensing device (as shown in FIG. 3) and secured to the dispensing device with the attachment 120. The roller ball 110 can be rolled over a surface, such as a user's skin, to apply a formula.

FIG. 2 is an example cross-section of an applicator 100, in accordance with the present technology. The applicator 100 may include a roller ball 110, an attachment 120, a reservoir 130 configured to hold a formula 140, a piston 150, a microcontroller 160, and a processor 170. In some embodiments, the applicator further includes a magnet 180. In some embodiments, the reservoir 130 is located inside the applicator 100, and is configured to hold a formula. In some embodiments, the formula is a skin care formula. In some embodiments, the skin care formula is a moisturizer, a toner, an acne treatment, a wrinkle treatment, fine line treatment, or a cosmetic. As the roller ball 110 rolls, formula 140 from the reservoir 130 is applied to a surface.

In some embodiments, the applicator 100 further includes a piston 150 configured to push the formula 140 towards the roller ball 110 as the formula is applied. In some embodiments, the piston 150 is directed by circuitry on a dispensing device or on the applicator itself to push the formula 140.

In some embodiments, the applicator 100 includes a microcontroller 160 configured to identify the type of formula 140 inside the applicator 100 to a dispensing device. In some embodiments, the microcontroller 160 further identifies the type of treatment the applicator should apply, i.e., the type of vibration treatment that should be applied with the type of formula 140. In some embodiments, the vibration treatment is continuous. In some embodiments, the vibration treatment is pulsed. In some embodiments, the vibration treatment is applied for a specific time amount, such as one minute, or five minutes. In some embodiments, the applicator stops administering vibration treatment when the specific time amount has elapsed. In some embodiments, the vibration treatment may be one of any number of intensities of frequency. The microcontroller 160 may also be used to identify any number of things about the formula 140 or applicator 100, including the amount of formula 140 inside the applicator 100, the expiration date of the formula 140 inside the applicator 100, or when to replace the applicator.

In some embodiments, the applicator 100 further includes a magnet 180 inside the roller ball 110. In some embodiments the magnet 180 is configured to respond to a magnetic field inside the applicator or inside a dispensing device (as shown in FIG. 3). In some embodiments, the magnet 180 is agitated to activate vibration in the roller ball 110. In some embodiments, the magnetic field is generated by a coil. In some embodiments, the coil is located inside the dispensing device, as shown in FIG. 3. In some embodiments, the coil is configured to agitate the magnet 180 in any number of intensities.

FIG. 3 is an example dispensing device, in accordance with the present technology. In some embodiments, the applicator 100 can be attached to a dispensing device 200. In some embodiments, the dispensing device includes an end 210, one or more light sources 220a, 220b, an actuator 230, a contactless reader 240, and a coil 250. In some embodiments, the applicator 100 connects to the dispensing device 200.

In some embodiments, the dispensing device 200 includes an end 210. The end 210 may be configured to be seen through the attachment 120 on the applicator 100. In some embodiments, the end 210 includes one or more light sources 220a, 220b configured to administer light therapy to a surface while the formula 140 is being applied.

In some embodiments, the one or more light sources 220a, 220b are LEDs. In some embodiments, there are only two light sources 220a, 220b on the dispensing device. In some embodiments, a first light source 220a is configured to administer light therapy in a first wavelength. In some embodiments, a second light source 220b is configured to administer light therapy in a second wavelength. In some embodiments, the light therapy in the first wavelength and the light therapy in the second wavelength are administered simultaneously. In some embodiments, the light therapy and applying the formula happen simultaneously. In some embodiments, there are one or more light sources 220a, 220b in a ring, located around the end 210 of the dispensing device 200.

In some embodiments, the dispensing device 200 includes one or more actuators 230. While the actuator is illustrated as a button, in some embodiments, the actuator may be a switch, a capacitive touch type button, a dial, or the like. The actuator may be configured to begin the administration of light therapy, to apply the formula, to control the vibration treatment, or all three. In some embodiments, the dispensing device 200 also includes a contact-less chip reader 240 to read the microcontroller 160 on the applicator 100.

In some embodiments, the dispensing device 200 further includes a coil 250 configured to generate a magnetic field to agitate a magnet in the roller ball of the applicator (as seen in FIG. 2). In some embodiments, the coil is configured to agitate the magnet in an intensity. In some embodiments, the coil 250 is configured to pulse the vibration by agitating the magnet in bursts. In some embodiments, the coil 250 is configured to vibrate the magnet continuously.

In operation, a user may place an applicator 100 into the dispensing device 200. When the actuator 230 is actuated, the formula is applied, the light therapy is administered, or both, simultaneously. A user may then apply the formula with the applicator 100. Additionally, the vibration treatment can be administered at the same time as the light therapy and applying the formula.

Figure 4:
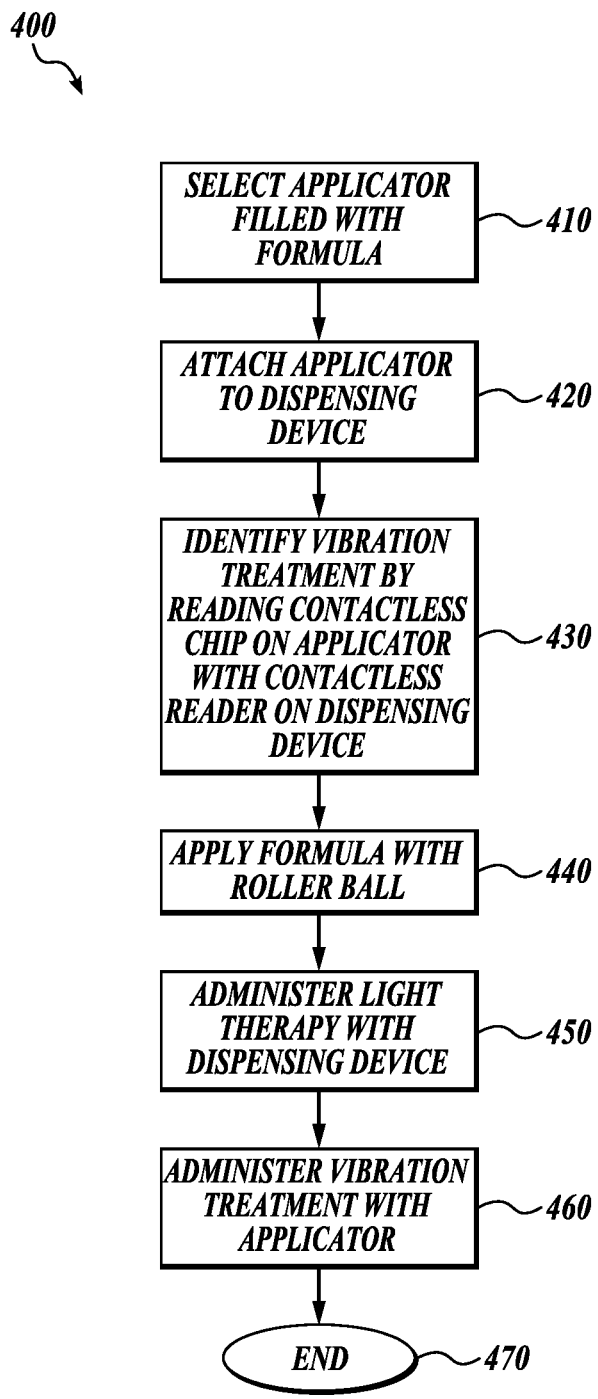
FIG. 4 is an example method of using a skin care system, in accordance with the present technology.

FIG. 4 is an example method of using a skin care system, in accordance with the present technology.

In block 410, an applicator is selected having a specific formula and configured to direct the applicator and/or the dispensing device to administer a specific vibration treatment. In some embodiments, the vibration treatment is continuous. In some embodiments, the vibration treatment is pulsed. In some embodiments, the vibration treatment is applied for a specific time amount, such as one minute, or five minutes. In some embodiments, the applicator stops administering vibration treatment when the specific time amount has elapsed. In some embodiments, the applicator further directs the applicator and/or the dispensing device to administer the vibration treatment at a specific intensity.

In block 420, the applicator is attached to the dispensing device. In some embodiments, the applicator is attached to the dispensing device with an attachment. In some embodiments, the applicator is clear to allow one or more light sources on the dispensing device to emit light through the attachment. In some embodiments, the applicator slides, clicks, or connects into the dispensing device. In some embodiments, the applicator attaches to the dispensing device with a threaded connection or a magnet.

In block 430, the dispensing device reads the microprocessor (or contactless chip) on the applicator with a contactless reader. In some embodiments, the microprocessor on the applicator identifies the type of formula, the type of vibration treatment to administer, the lifetime of the applicator, the amount of formula inside the applicator, or a combination thereof.

In block 440, formula is applied as the roller ball is rolled along a surface. In some embodiments, the surface is a user's face. In some embodiments, the surface may be any portion of the user's skin.

In block 450, light therapy is applied with the dispensing device. In some embodiments, the dispensing device includes an actuator configured to begin both the application of the formula and the administration of the light therapy. In some embodiments, the dispensing device includes two or more light sources configured to administer the light therapy. In some embodiments, the dispensing device is configured to deliver two or more types of light therapy, either one at a time, or simultaneously. In such embodiments, one light source is configured to administer a first light therapy, and another light source is configured to administer a second light therapy. In some embodiments, the first light therapy may include emitting a first light at a first wavelength, and the second light therapy may include emitting a second light at a second wavelength.

In block 460, the vibration treatment is applied with the applicator. In some embodiments, blocks 440, 450, and 460 occur simultaneously. In some embodiments, the method further includes removing the applicator and placing a second applicator into the dispensing device to administer a second vibration treatment and/or a second formula.

In block 470, the method ends.

The embodiments of the invention in which an exclusive property or privilege is claimed are defined as follows:

1. A skin care system comprising:
   a dispensing device configured to administer a light therapy and a vibration treatment; and
   an applicator configured to apply a formula, comprising:
   a reservoir configured to hold the formula,
   a roller ball configured to apply the formula,
   a magnet located in the roller ball,
   a coil, wherein the coil is configured to agitate the magnet to apply vibration treatment,
   a connection configured to attach the applicator to the dispensing device, and
   a microcontroller configured to direct the dispensing device to apply the vibration treatment, wherein the light therapy and the vibration treatment are administered simultaneously with the application of the formula.

2. The skin care system of claim 1, wherein the dispensing device is configured to apply two or more wavelengths of light therapy simultaneously.

3. The skin care system of claim 1, wherein the dispensing device administers light therapy through one or more light sources.

4. The skin care system of claim 3, wherein the one or more light sources are a ring of LEDs around a top of the dispensing device.

5. The skin care system of claim 3, wherein the applicator further comprises a clear attachment so that the light from the one or more light sources on the dispensing device can pass through the attachment to administer the light therapy.

6. The skin care system of claim 1, wherein the coil is located inside the dispensing device.

7. The skin care system of claim 6, wherein the vibration treatment is selected from constant vibration or pulsed vibration.

8. The skin care system of claim 1, wherein the dispenser is further configured to control the intensity of the vibration treatment.

9. A method of administering multiple skin treatments, using the system of claim 1, the method comprising:
selecting an applicator filled with a formula;
placing the applicator into the dispensing device;
identifying a vibration treatment to apply based on the applicator;
applying the formula;
administering light therapy; and
administering the vibration treatment.

10. The method of claim 9, wherein applying of the formula, the administering the light therapy, and administering the vibration treatment is done simultaneously.

11. The method of claim 9, wherein the dispensing device administers light treatment through one or more light sources.

12. The method of claim 11, wherein the one or more light sources are a ring of LEDs around a top of the dispensing device.

13. The method of claim 9, wherein the method further comprises identifying the formula in the applicator with the dispensing device.

14. The method of claim 9, wherein the method further comprises removing the applicator and placing a second applicator into the dispensing device to administer a second vibration treatment and/or a second formula.

15. The method of claim 9, wherein the method further comprises:
applying voltage to the coil inside an applicator; and
agitating the magnet in the roller ball of the applicator to administer vibration treatment.

16. The method of claim 9, wherein the method further configures adjusting the intensity of the vibration treatment with the dispensing device.

17. The method of claim 9, wherein the method further comprises applying the vibration treatment for a specific time amount based on the microcontroller of the applicator.

18. The method of claim 9, wherein the method further comprises stopping the vibration treatment when the specific time amount has elapsed.

* * * * *

UNITED STATES PATENT AND TRADEMARK OFFICE
CERTIFICATE OF CORRECTION

Page 1 of 1

PATENT NO. : 12,089,716 B2
APPLICATION NO. : 17/733270
DATED : September 17, 2024
INVENTOR(S) : Gregoire Charraud et al.

It is certified that error appears in the above-identified patent and that said Letters Patent is hereby corrected as shown below:

On the Title Page

| Column | Line | |
|---|---|---|
| 2 | 2 | Item (74), under "Attorney, Agent, or Firm", delete "O'CONNER" and insert -- O'CONNOR -- |

Signed and Sealed this
Eleventh Day of February, 2025

Coke Morgan Stewart
*Acting Director of the United States Patent and Trademark Office*